United States Patent
Bartha et al.

(10) Patent No.: US 9,023,838 B2
(45) Date of Patent: May 5, 2015

(54) CRYSTALLINE FORM I ROSUVASTATIN ZINC SALT

(75) Inventors: Ferenc Bartha, Tiszavasvari (HU); Gyoergyi Kovanyine Lax, Budapest (HU); Balazs Volk, Budapest (HU); Jozsef Barkoczy, Budapest (HU); Gyoergy Morovjan, Budapest (HU); Gyoergy Krasznai, Budapest (HU); Kalman Nagy, Budapest (HU); Gyula Simig, Budapest (HU); Gyoergy Ruzsics, Hoegyesz (HU); Gyoergy Clementis, Budapest (HU); Imre Kapui, Erd (HU); Peter Slegel, Budapest (HU); Adrienn Keszthelyi, Budapest (HU); Zsuzsanna Szent-Kirallyi, Budapest (HU); Valeria Hoffmanne Fekete, Budapest (HU); Janos Imre, Budapest (HU)

(73) Assignee: Egis Gyogyszergyar Nyilvanosan Muekoedoe, Budapest (HU)

( * ) Notice: Subject to any disclaimer, the term of this patent is extended or adjusted under 35 U.S.C. 154(b) by 191 days.

(21) Appl. No.: 13/383,490

(22) PCT Filed: Jul. 24, 2009

(86) PCT No.: PCT/HU2009/000064
§ 371 (c)(1),
(2), (4) Date: Mar. 29, 2012

(87) PCT Pub. No.: WO2011/010174
PCT Pub. Date: Jan. 27, 2011

(65) Prior Publication Data
US 2012/0178729 A1    Jul. 12, 2012

(51) Int. Cl.
*A61K 31/506*    (2006.01)
*C07D 239/02*    (2006.01)
*C07D 239/42*    (2006.01)

(52) U.S. Cl.
CPC ................................ *C07D 239/42* (2013.01)

(58) Field of Classification Search
CPC ........................ A61K 31/506; C07D 239/42
USPC ........................................ 514/184; 544/226
See application file for complete search history.

(56) References Cited

U.S. PATENT DOCUMENTS

2009/0306117 A1    12/2009    Vago et al.

FOREIGN PATENT DOCUMENTS

| WO | WO 2008/015563 | 2/2008 |
| WO | WO 2009/047576 | 4/2009 |
| WO | WO 2009/047577 | 4/2009 |

*Primary Examiner* — James O Wilson
*Assistant Examiner* — Ebenezer O Sackey
(74) *Attorney, Agent, or Firm* — Lucas & Mercanti, LLP; Jonathan Myers

(57) ABSTRACT

The present invention relates to crystalline Form I rosuvastatin zinc (2:1) salt, method of preparation thereof and use thereof as pharmaceutically active ingredient for the treatment of diseases related to lipid metabolism including hyperlipoproteinemia, hypercholesteremia, dyslipidemia and atherosclerosis.

22 Claims, 1 Drawing Sheet

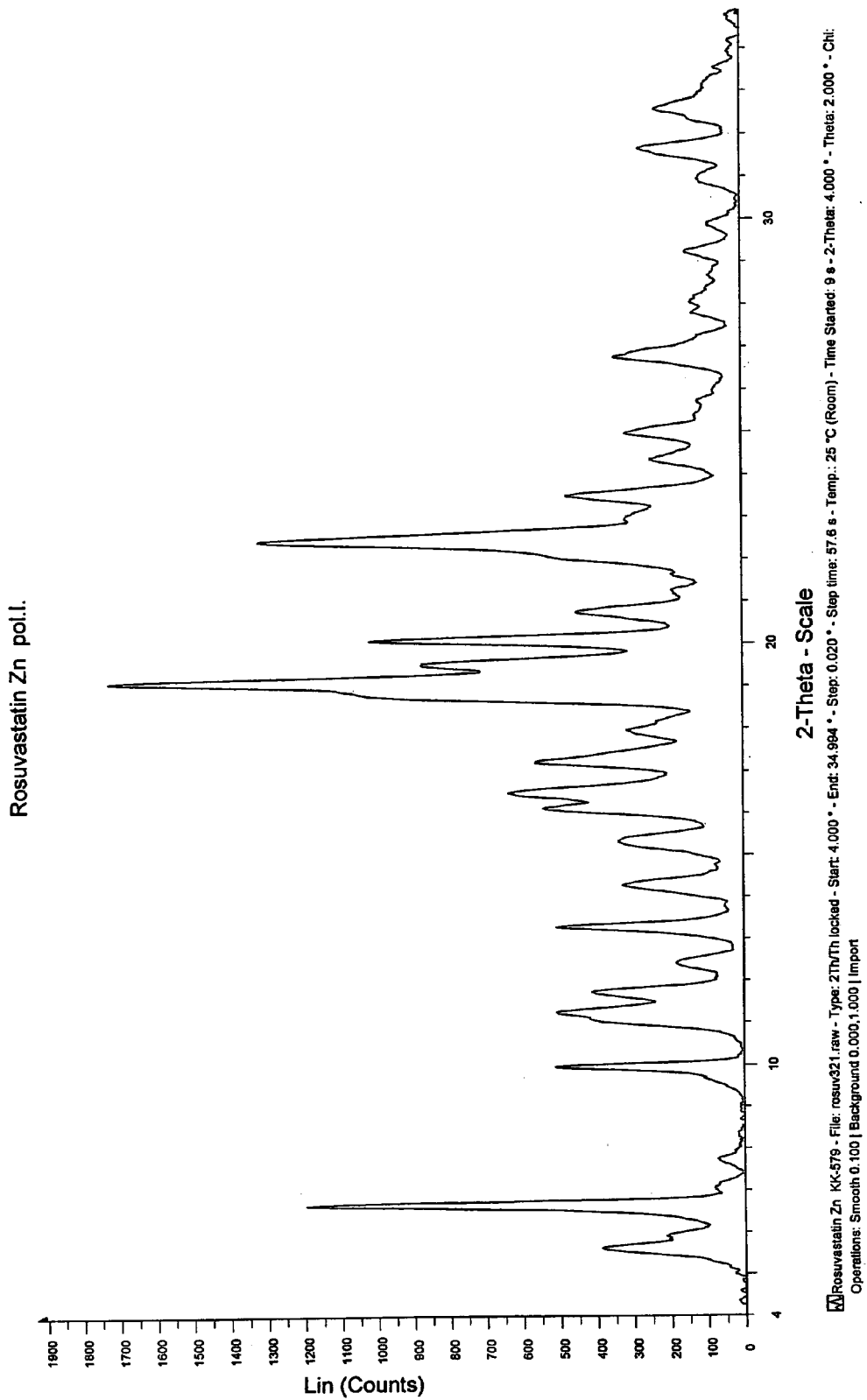

CRYSTALLINE FORM I ROSUVASTATIN ZINC SALT

CROSS REFERENCE TO RELATED APPLICATION

This application is the US National stage of PCT application PCT/HU2009/000064 filed 24 Jul. 2009, published 27 Jan. 2011 as WO 2011/010174.

FIELD OF THE INVENTION

The present invention relates to crystalline zinc salt of (+)-7-[4-(4-fluorophenyl)-6-isopropyl-2-(methanesulfonyl-methyl-ainino) pyrimidin-5-yl]-(3R,5.S)-dihydroxy-hept-6-enoic acid of the Formula (I)-

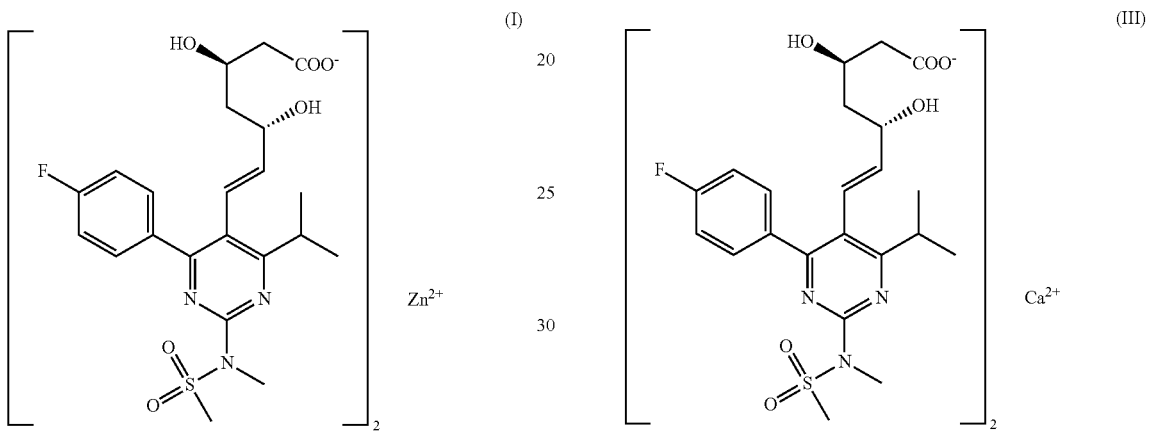

The compound (+)-744-(4-fluorophenyl)-6-isopropyl-2-(methanesulfonyl-methyl-amino)-pyrimidin-5-yl]-(3R,55)-dihydroxyhept-6-enoic acid of the Formula (II)

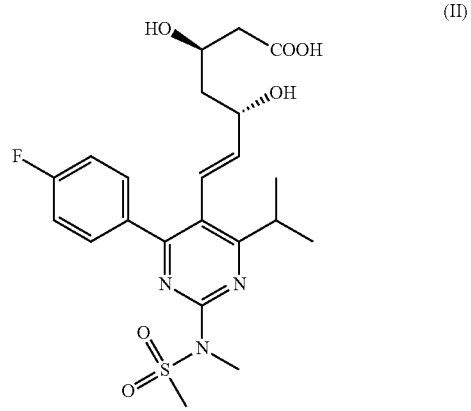 [SMILES: CC(C)c1nc(N(C)S(C)(=O)=O)nc(-c2ccc(F)cc2)c1/C=C/[C@@H](O)C[C@@H](O)CC(=O)O]

is known by the International Nonproprietary Name rosuvastatin and used in the medicine as a pharmaceutically active ingredient for the treatment of the disorders of the lipid metabolism. Rosuvastatin exerts its activity by inhibiting 2-methyl-glutaryl-coenzyme A reductase present in the liver, thus decreasing the rate of the cholesterol biosynthesis in the liver and the cholesterol concentration of the blood. Rosuvastatin, mostly in the form of salts thereof, can be used for the treatment of hypercholesterolemia, hyperlipoproteinemia and atherosclerosis.

The subject of the present invention is crystalline Form I of (+)-7-[4-(4-fluorophenyl)-6-isopropyl-2-(methanesulfonyl-methyl-amino)-pyrimidin-5-yl]-(3R,5S)-dihydroxy-hept-6-enoic acid zinc (2:1) salt, method for preparation thereof and use thereof in the manufacture of medicaments.

BACKGROUND OF THE INVENTION (+)-7-[4-(4-fluorophenyl)-6-isopropyl-2-(methanesulfonyl-methylamino)-pyrimidin-5-yl]-(3R,5S)-dihydroxy-hept-6-enoic acid of the Formula (II) (rosuvastatin) is known from the state of the art. Rosuvastatin has been disclosed for the first time in European Patent No. 521471 as the free acid and some pharmaceutically acceptable salts thereof, such as the calcium salt of the Formula (III)

and ammonium salt. Published International Patent Application WO 01/060804 discloses crystalline lithium, magnesium salts of rosuvastatin and crystalline salts of the compound with certain amines. In the Published International Patent Applications WO 2005023779, WO 2006079611 and WO 2008036286, several different crystalline hydrate forms of rosuvastatin calcium of the Formula (III) are disclosed. International Patent Applications WO 2005051921 and W02008038132 are related to further salts or rosuvastatin with amines or diamines. International Patent Application WO 2005077917 discloses amorphous rosuvastatin magnesium salt. Published International Patent Application WO 2007086082 discloses the amorphous and crystalline potassium salt and the method for preparation thereof.

Rosuvastatin zinc (2:1) salt of the Formula (I) has been disclosed for the first time in Hungarian Patent Application P0600293 and in the corresponding International Patent Application WO 2007119085. Hungarian Patent Application P070667 and the corresponding Published International Patent Application WO 2009047577 is related to further methods for the preparation of rosuvastatin zinc salt of the Formula (I), wherein rosuvastatin of the Formula (II), sodium salt thereof, an alkyl ester thereof, rosuvastatin lactone or rosuvastatin ketal ester are used as starting materials.

In the International Patent Application WO 2008015563, a method for the preparation of rosuvastatin zinc salt of the Formula (I) has been disclosed, which comprises transforming rosuvastatin tert-butylamine salt into rosuvastatin sodium salt and producing the zinc salt by reacting said rosuvastatin sodium salt with zinc ions and filtering the product from an aqueous solvent.

Hungarian Patent Application P0900019 is related to a further method for the preparation of rosuvastatin zinc salt of the Formula (I), wherein rosuvastatin zinc salt of the Formula (I) is produced directly starting from the tert-butylamine salt of rosuvastatin and isolating said product from an organic solvent.

Rosuvastatin zinc salt of the Formula (I) obtained by the methods of Hungarian Patent Applications P0600293, P070667 and P0900019 or by the method disclosed in International Patent Application WO 2008015563 is of amorphous morphology. No crystalline form of rosuvastatin zinc salt of the Formula (I) are known according to the state of the art.

The quality of the pharmaceutically active ingredient used in medicinal product are determined by strict criteria set forth by health authorities. Some of these criteria is related to the chemical purity and stability of the active ingredient. Further criteria apply to the quality and stability of the medicinal product. These criteria are set forth and published in pharmacopoeias. A basic condition for the issue of the marketing authorization is the compliance with the quality requirements regarding pharmaceutically active ingredients as well as medicinal products.

During the use of rosuvastatin for the manufacture of medicaments, there exists a need for obtaining the pharmaceutically active ingredient in high purity, being chemically stabile and in a form which can be easily manipulated during the manufacture of the medicinal product.

Recently a definite need has arisen in the pharmaceutical industry for reproducible manufacturing methods for obtaining pharmaceutically active ingredients in chemically and morphologically pure form. Obtaining the pharmaceutically active ingredient in homogeneous solid state is a precondition for complying with the requirements of the industrial manufacture of finished dosage forms. It is a well known fact that solid forms of the same active ingredient having different morphology may exhibit significant differences in the rate of dissolution, bioavailability and chemical stability. From the viewpoint of industrial chemical and pharmaceutical technology, it is important that different solid forms of an active ingredient can possess significantly different properties with regard to the operations of the technology, e.g. rate of filtration or drying, solubility, behavior during tabletting. The properties mentioned above have direct impact on the efficiency, economy, reproducibility and complexity of the industrial manufacturing process and at the same time, results in a morphologically homogeneous product.

It is generally accepted that crystalline forms of pharmaceutically active ingredients possess enhanced chemical stability as compared to the amorphous form. Due to the different decomposition processes during the manufacture and shelf-life of the finished dosage form, this assumption is of general importance. Therefore, manufacturers of medicinal products prefer to use crystalline forms of the active ingredients during pharmaceutical development.

Active ingredients belonging to the group of statins are explicitly prone to decomposition (Ravi P. Shah, Vijay Kumar and Saranjit Singh, LC-MS/MS Studies on Identification and Characterization of Hydrolytic Products of Atorvastatin, Proceedings of 12th ISMAS Symposium cum Workshop on Mass Spectrometry, Mar. 25-30, 2007, Cidade de Goa, Dona Paula, Goa), thus there exists a need to provide forms of the active ingredients belonging to this group which exhibit enhanced chemical stability. For example, it is known that amorphous form of atorvastatin having similar structure to rosuvastatin (i.e. both compounds share the 3,5-dihydroxy-alkanoic acid moiety) or even the morphologically non-homogeneous mixture of amorphous and crystalline forms disclosed in European Patent 409281 are less stable than crystalline forms thereof. Thus, development of crystalline forms I, II and IV showing enhanced properties during chemical or pharmaceutical manipulations (e.g. ease of filtration) and increased stability as disclosed in Published International Patent Application WO 97/03959, initiated development work on behalf of several companies resulting in the development of more than forty crystalline forms of atorvastatin.

Rosuvastatin is especially prone to decomposition resulting from exposure to light, oxygen and heat. For example, upon light exposure, decomposition products described by Astrarita and coworkers are formed even in solid state (J. Photochem. Photobiol. A. Chem. 2007, 187, 263-268).

OBJECT OF THE INVENTION

According to the above-mentioned facts, there is a strong need to provide crystalline salts of rosuvastatin of the Formula (II).

The objective of our research-development work was to provide rosuvastatin zinc (2:1) salt in crystalline form, which is amenable to the manufacture of medicaments and can be produced consistently in high quality under industrial conditions.

SUMMARY OF THE INVENTION

The above objective is achieved according to the present invention.

We have found surprisingly that rosuvastatin zinc (2:1) salt can be synthesized in morphologically homogeneous crystalline form, which has suitable stability and physicochemical properties and which can be manufactured reproducibly on an industrial scale using a simple process. This observation is unexpected since all known methods for the manufacture of rosuvastatin zinc (2:1) salt result always in an amorphous product and because all earlier attempts to crystallize rosuvastatin zinc (2:1) salt failed.

Furthermore, it is known that crystalline forms of rosuvastatin calcium, disclosed for the first time in 1991, have been available since more than 10 years after the discovery of the amorphous form. Despite the fact that crystalline forms of rosuvastatin calcium have been prepared, said crystalline forms are still not used for the manufacture of medicaments. This phenomenon is reflected in the fact that even the originator product CRESTOR® contains rosuvastatin calcium in amorphous form.

It is surprising that the zinc (2:1) salt of rosuvastatin can be produced in crystalline form since the formation of complexes of the transitional metal zinc with organic ligands as well as water, is well known.

Furthermore, there is no method in the state of the art which could be used for predicting the chances of crystal formation for a chemical compound or a salt known only in amorphous form.

According to the first aspect of the present invention, there is provided crystalline Form I of (+)-7-[4-(4-fluorophenyl)-6-isopropyl-2-(methanesulfonyl-methyl-amino)-pyritnidin-5-yl]-(3R,58)-dihydroxyhept-6-enoic acid zinc (2:1) salt of the Formula (I).

According to the second aspect of the present invention, there are provided methods for the manufacture of crystalline Form I rosuvastatin zinc (2:1) salt.

According to the third aspect of the invention, there are provided methods for the use of crystalline Form I rosuvastatin zinc (2:1) salt of the Formula (I) for the manufacture of medicaments.

A further aspect of the present invention is the use of crystalline Form I rosuvastatin zinc (2:1) salt for the treatment of the disorders associated with impaired cholesterol and lipid metabolism.

DETAILED DESCRIPTION OF THE INVENTION

The prior art is silent about crystalline forms of rosuvastatin zinc (2:1) salt. All disclosure in the prior art is related to amorphous rosuvastatin zinc (2:1) salt. Rosuvastatin zinc (2:1) salt of the Formula (I) produced according to the method disclosed in Hungarian Patent Applications P0600293, P070667 and P0900019 does not have sharp, well-defined melting point. The melting begins at 137° C. and occurs over a wide temperature range. Rosuvastatin zinc (2:1) salt obtained by the method of International Patent Application WO 2008015563 is characterized by powder X-ray diffraction analysis. The analytical results disclosed in said patent application clearly indicate that the product obtained has amorphous morphology. No melting point has been disclosed.

According to the first aspect of the present invention, there is provided crystalline Form I of (+)-7-[4-(4-fluorophenyl)-6-isopropyl-2-(methanesulfonyl-methyl-amino)-pyrimidin-5-yl]-(3R,5S)-dihydroxyhept-6-enoic acid zinc salt (2:1) of the Formula (I). Crystalline Form I rosuvastatin zinc (2:1) salt is new.

BRIEF DESCRIPTION OF THE DRAWING

FIG. 1 is a powder x-ray diffractogram of crystalline Form I of rosuvastatin zinc (2:1) salt.

The powder X-ray diffraction pattern characteristic for the crystalline Form I rosuvastatin zinc salt (2:1) measured using CuKc, radiation is shown in FIG. 1. Characteristic X-ray diffraction angles and the corresponding relative intensities exceeding 5% are given in Table 1 below.

TABLE 1

Diffraction data of crystalline Form I rosuvastatin zinc (2:1) salt

| Peak No. | 2Θ | d (Å) | Relative intensity (%) |
|---|---|---|---|
| 1 | 5.584 | 15.81321 | 22.2 |
| 2 | 5.889 | 14.99555 | 12.1 |
| 3 | 6.621 | 13.33946 | 69.1 |
| 4 | 7.038 | 12.55036 | 5.1 |
| 5 | 9.920 | 8.90897 | 29.4 |
| 6 | 11.072 | 7.98468 | 24.4 |
| 7 | 11.213 | 7.88447 | 29.5 |
| 8 | 11.679 | 7.57108 | 23.6 |
| 9 | 12.391 | 7.13765 | 10.4 |
| 10 | 13.248 | 6.67775 | 29.2 |
| 11 | 14.266 | 6.20332 | 18.7 |
| 12 | 15.311 | 5.78220 | 19.4 |
| 13 | 16.127 | 5.49159 | 31.1 |
| 14 | 16.471 | 5.37744 | 36.6 |
| 15 | 17.230 | 5.14225 | 32.2 |
| 16 | 17.936 | 4.94151 | 17.9 |
| 17 | 18.756 | 4.72726 | 59.1 |
| 18 | 19.089 | 4.64561 | 100 |
| 19 | 19.505 | 4.54752 | 50.5 |
| 20 | 20.074 | 4.41990 | 58.8 |
| 21 | 20.738 | 4.27984 | 25.9 |
| 22 | 21.217 | 4.18430 | 11 |
| 23 | 21.620 | 4.10713 | 11.3 |
| 24 | 22.101 | 4.01878 | 31.4 |
| 25 | 22.466 | 3.95434 | 76.3 |
| 26 | 22.968 | 3.86898 | 18.2 |
| 27 | 23.499 | 3.78272 | 27.4 |
| 28 | 24.372 | 3.64924 | 14 |
| 29 | 25.001 | 3.55888 | 18 |
| 30 | 25.751 | 3.45684 | 6.7 |
| 31 | 26.806 | 3.32318 | 19.7 |
| 32 | 27.243 | 3.27079 | 7.2 |
| 33 | 27.828 | 3.20337 | 7.8 |
| 34 | 28.171 | 3.16516 | 7.2 |
| 35 | 29.239 | 3.05194 | 8.5 |
| 36 | 29.885 | 2.98740 | 4.9 |
| 37 | 30.971 | 2.88504 | 6.5 |
| 38 | 31.655 | 2.82424 | 15.7 |
| 39 | 32.635 | 2.74171 | 13.1 |

Measurement conditions for the powder X-ray diffraction analysis were the following:
Instrument: BRUKER D8 ADVANCE powder X-ray diffractometer
Radiation: $Cu_{K\alpha}$ (=1.54060 A), $Cu_{K\alpha 2}$ (?=1.54439 A)
Voltage: 40 kV
Anode current: 30 mA
Accessories: Gdbel-mirror, Soller-slit, sampler, transmission position
Detector: LynxEye
Measurement: continuous Θ/Θ scan: 4°-35° 2Θ
Step: 0.02°
Sample: without pretreatment, room temperature
Reproducibility: ±0.2° 2Θ

It is well known from the state of the art that pretreatment of the sample (e.g. pulverization) can have very significant effect on the relative intensities of the powder X-ray diffractogram. Therefore, no pretreatment of the sample was applied.

The person skilled in the art is in the position to identify the solid-state morphology of a known substance by the powder X-ray diffractograms. This can be carried out simply by determining the position (diffraction angle) of a few intense X-ray diffraction signals. Such an identification is very important for the testing of the morphology of the active ingredient in solid dosage forms, since during the manufacture of the solid finished dosage form, changes of morphology may occur either by transformation of the crystalline active ingredient into a different crystalline form or into the amorphous form.

The diffraction angles belonging to the most intense diffraction signals of the crystalline Form I rosuvastatin zinc salt (2:1) are 6.621, 19.089 and 22.466 degrees 2Θ. These X-ray diffraction signals can be most conveniently used for the identification of crystalline Form I of rosuvastatin zinc (2:1) salt.

Diffraction angles of the diffraction lines where the relative intensity exceeds 50% in the diffractogram of crystalline Form I rosuvastatin zinc (2:1) salt are 6.621; 18.756; 19.089; 19.505; 22.466 degrees 2Θ.

Diffraction angles belonging to the diffraction signals of crystalline Form I of rosuvastatin zinc (2:1) salt having at least 20% relative intensity are the following: 6.621; 9.920; 11.213; 13.248; 16.127; 16.471; 17.230; 18.756; 19.089; 19.505; 22.101; 22.466 degrees 2Θ.

Crystalline morphology of Form I rosuvastatin zinc salt (2:1) established by the powder X-ray diffractogram described above is further confirmed by the fact that said crystalline Form I rosuvastatin zinc salt (2:1) has a sharp melting point of 119-121° C.

Crystalline Form I rosuvastatin zinc salt (2:1) of the present invention can contain 1 to 10 molar equivalents of water either in form of hydrate water or as physically adsorbed water. Although physicochemical test results suggest that crystalline Form I rosuvastatin zinc salt (2:1) predominantly contains 1 to 6 molar equivalents of water, it has been established that said substance containing higher amount of water is also acceptable for the manufacture of finished dosage forms.

According to the second aspect of the present invention, there are provided methods for the preparation of crystalline Form I rosuvastatin zinc (2:1) salt of the Formula (I).

Preferably all manipulations are carried out in inert gas atmosphere.

Crystalline Form I rosuvastatin zinc salt (2:1) of the present invention can be produced by suspending amorphous rosuvastatin zinc salt (2:1) in 5 to 100-fold weight of water at the temperature of 0 to 25° C., stirring the suspension for 4 to 168 hours, and isolating the product.

According to the preferable embodiment of the process, crystalline Form I rosuvastatin zinc salt (2:1) is produced by suspending amorphous rosuvastatin zinc salt (2:1) in 20-fold weight of water at a temperature of 0 to 5° C., stirring the suspension for 4 to 8 hours, collecting the solids by filtration or centrifugation, washing the solids with water and drying the product.

According to a second method for the preparation of crystalline Form I rosuvastatin zinc (2:1) salt, a suspension of amorphous rosuvastatin zinc salt (2:1) in 5 to 100-fold, preferably 20-fold weight of water is provided at a temperature between 0 and 25° C., preferably at 0 to 5° C., said suspension is stirred at the same temperature for 2 to 168 hours, preferably for 4 to 8 hours, the solids are recovered and washed once or several times with water, and subsequently the thus obtained solids are suspended in 5 to 100-fold, preferably in 20-fold weight of water at 0 to 25° C., preferably at 0 to 5° C., the suspension is stirred for 1 to 168 hours, preferably for 2 to 4 hours at the same temperature and the solid is isolated, washed and dried.

The third method for the preparation of crystalline Form I rosuvastatin zinc salt (2:1) of the present invention comprises suspending amorphous rosuvastatin zinc salt (2:1) in 5 to 100-fold, preferably 20-fold weight of water containing 0.0005 to 0.01 molar equivalent, preferably 0.005 molar equivalent alkali metal hydroxide, preferably sodium hydroxide calculated for the molar amount of rosuvastatin zinc salt of the Formula (I), at the temperature of 0 to 25° C., preferably at 20° C., stirring the thus obtained suspension for 4 to 168 hours, preferably 4 to 8 hours at the same temperature, recovering and optionally washing and drying the solid crystalline Form I rosuvastatin zinc salt (2:1).

A further method for the preparation of rosuvastatin zinc salt (2:1) in crystalline Form I comprises suspending amorphous rosuvastatin zinc salt (2:1) in 5 to 100-fold, preferably 20-fold weight of water containing 0.0005 to 0.01 molar equivalent, preferably 0.005 molar equivalent alkali metal hydroxide, preferably sodium hydroxide, calculated for the molar amount of rosuvastatin zinc salt of the Formula (I) at the temperature of 0 to 25° C., preferably at 20° C., stirring the thus obtained suspension for 4 to 168 hours, preferably 4 to 8 hours at the same temperature, isolating and optionally washing the solid with water or with 0.0005 to 0.01 molar alkali metal hydroxide, preferably sodium hydroxide solution and suspending the solids repeatedly under the same conditions for 1 to 168 hours, preferably for 2 to 4 hours, recovering and optionally washing and drying the crystalline Form I rosuvastatin zinc (2:1) salt.

According to a still further process, crystalline Form I rosuvastatin zinc salt (2:1) can be produced by suspending amorphous rosuvastatin zinc salt (2:1) in the mixture of water and isopropyl acetate at a temperature between 0 and 30° C., preferably at room temperature, stirring the suspension for 4 to 168 hours and isolating the product by filtration and optionally washing and drying the crystalline Form I zinc (2:1) salt.

We have found that crystalline Form I rosuvastatin zinc salt (2:1) is more advantageous with respect to chemical stability than the amorphous form known from the art.

Chemical stability of the pharmaceutically active ingredient is an important feature since there are existing expectations by which the concentration of impurities in the finished dosage form should not increase significantly during their shelf-life (1-2 years). Furthermore, there exist official requirements which compel the manufacturer carrying out separate toxicology study with regard to impurities of known structure if the concentration of such an impurity exceeds the limit concentration of 0.15%.

Chemical stability of amorphous and crystalline Form I rosuvastatin zinc salts (2:1) has been determined by challenging said substances at the storage condition of 25° C., 60% relative humidity. The results of the test are shown in Table 2. The concentration of the two most significant impurities, 7-[4-(4-fluorophenyl)-6-(1-methylethyl)-2-[methyl-methylsulfonyl-amino]-5-pyrimidinyl]-3-hydroxy-5-oxo-(3R,5R, 6E)-6-heptenoic acid (5-oxo derivative, referred to as impurity M-2) of the Formula (IV)

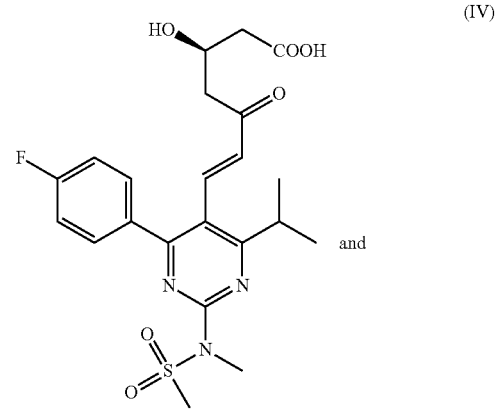 [SMILES: CC(C)c1nc(N(C)S(C)(=O)=O)nc(-c2ccc(F)cc2)c1/C=C/C(=O)C[C@@H](O)CC(=O)O]

and

N-(4-(4-fluorophenyl)-5-{(E)-2-[{2S'4R)-4-hydroxy-2-oxo-tetrahydro-2H-pyran-2-yl]ethenyl}-6-isopropyl-pyrimidin-2-yl)-methylmethanesulfonamide (rosuvastatin lactone) of the Formula (V)

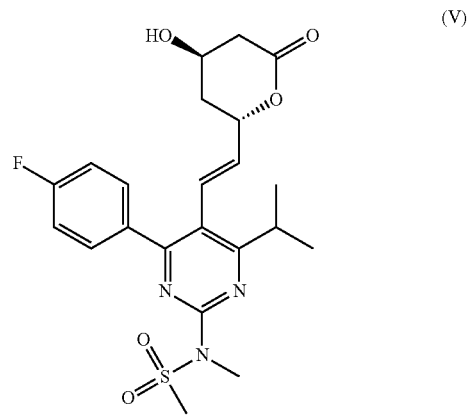 [SMILES: CC(C)c1nc(N(C)S(C)(=O)=O)nc(-c2ccc(F)cc2)c1/C=C/[C@@H]1C[C@@H](O)CC(=O)O1]

has been increased much more significantly in the product of amorphous morphology than in the crystalline Form I zinc salt of the present invention.

It has been established that the concentration of impurity M-2 increases already in one month under the long-term stability testing condition (25° C., 60% relative humidity) to three-fold of the initial concentration in the amorphous form of rosuvastatin zinc salt. In comparison, the concentration of the same impurity in the crystalline Form I substance stored under the same conditions is practically unchanged, i.e. it is within the repeatability of the assay method.

Similarly, it has been found that crystalline Form I of rosuvastatin zinc salt (2:1) is much less prone to form lactone of rosuvastatin, than the amorphous zinc salt. Even though the lactones of statins are considered to be non-toxic impurities of statins, five-fold increase in the concentration of rosuvastatin lactone, as observed in the case of amorphous rosuvastatin zinc salt (2:1) after one month storage, is a ground for quality concerns due to the decrease of the amount of the active ingredient.

We have furthermore found that during the storage of crystalline Form I rosuvastatin zinc salt, the total amount of the impurities as well as the number of the individual impurities (as chemical entities) is significantly lower than that of the amorphous form.

An important advantage of crystalline Form I rosuvastatin zinc salt (2:1) resides in the fact that said form is much less hygroscopic than the amorphous form, which is advantageous for the reasons of stability and for the sake of simplicity of pharmaceutical manufacturing. It has been found that while amorphous rosuvastatin zinc salt (2:1) absorbed 1.88% by weight of water, the amount of water absorbed was only 0.24% by weight for the crystalline Form I rosuvastatin zinc salt (2:1) according to the present invention.

TABLE 2

Comparative stability data of crystalline Form I and amorphous rosuvastatin zinc (2:1) salt

| 25° C., 60% RH | Amorphous | | Form I | |
|---|---|---|---|---|
| | Initial | 1 month | Initial | 1 month |
| M-2 impurity | 0.03% | 0.10% | 0.07% | 0.08% |
| Lactone impurity | 0.10% | 0.51% | 0.13% | 0.32% |
| Total impurities | 0.38% | 0.77% | 0.28% | 0.49% |
| | (7 peaks) | (6 peaks) | (3 peaks) | (3 peaks) |

According to a further aspect of the present invention, there are provided medicaments containing crystalline Form I rosuvastatin zinc (2:1) salt of the Formula (I). Such medicaments may also contain one or more known vehicles or auxiliary agents.

The medicament according to the present aspect of the invention in most cases contains 0.1 to 95% by weight of pharmaceutically active ingredient of the Formula (I). The proportion of the active ingredient is advantageously between 5 to 75% by weight.

Medicaments according to the present invention can be administered orally (e.g. powders, tablets, coated or film-coated tablets, capsules, microcapsules, granules, pellets, dragees, solutions, suspensions or emulsions), parenterally (in the form of e.g. intravenous, intramuscular, subcutaneous or intraperitoneal injections or as an infusion), rectally (e.g. in the form of suppositories) or locally (e.g. as creams, ointments or patches). Solid, semisolid or liquid medicaments according to the present invention can be produced according to methods known from the prior art.

Medicaments suitable for oral administration containing crystalline Form I of rosuvastatin zinc salt (2:1) of the Formula (I) can be presented in solid form, which can contain one or more vehicle or filler (e.g. lactose, glucose, starch, calcium phosphate, microcrystalline cellulose), a binder (e.g. gelatine, sorbitol, polyvinylpyrrolidone), a disintegrant (e.g. croscarmellose, sodium carboxymethylcellulose, crospovidone), tabletting auxiliary agents (e.g. magnesium stearate, talc, polyethylene glycol, silica or silicon dioxide) or surfactants (e.g. sodium lauryl sulfate) besides the active ingredient.

Liquid medicaments intended for oral use containing crystalline Form (I) of rosuvastatin zinc salt (2:1) according to the present invention can be presented as solutions, suspensions or emulsions and can contain suspending agents (e.g. gelatine, carboxymethylcellulose), emulsifying agents (e.g. sorbitane monooleate), solvents or liquid vehicles (e.g. water, oils, glycerol, propylene glycol, ethanol), pH adjusting agents (e.g. acetate, phosphate, citrate buffers) or stabilizing agents (e.g. methyl 4-hydroxybenzoate) admixed with the active ingredient.

Medicaments containing the crystalline Form I of the compound of the Formula (I) intended for parenteral use are usually sterile isotonic aqueous solutions or suspensions, which can contain a pH adjusting agent and conservants as auxiliary agents.

Medicaments presented as semisolid formulations containing crystalline Form I of the compound of the Formula (I), such as suppositories contain the active ingredient homogeneously dispersed in the semisolid base (e.g. polyethylene glycol, cocoa butter).

Medicaments containing crystalline Form I of rosuvastatin zinc (2:1) salt according to the present invention can be produced as modified release, controlled-release or extended-release formulations. In this manner, long-lasting effect can be achieved or the intervals between the administration of the medicament can be increased. The modified release, controlled release or extended release medicaments can be produced according to the methods known from the prior art.

According to a further aspect of the present invention, there is provided a method for the manufacture of medicaments containing crystalline Form I of rosuvastatin zinc (2:1) salt of the Formula (I), which comprises admixing said crystalline Form I of rosuvastatin zinc (2:1) salt with a pharmaceutically acceptable vehicle and an auxiliary agent and transforming the thus obtained mixture into a pharmaceutical dosage form using the methods known in the art. Suitable pharmaceutically acceptable vehicles and auxiliary agents, as well as formulation methods have been disclosed in the prior art (Remington's Pharmaceutical Sciences, 18th Edition, Mack Publishing Co., Easton, USA, 1990).

Medicaments containing crystalline Form I of the compound of the Formula (I) contain the active ingredient in unit dosage forms.

According to a further aspect of the present invention, there is provided a method for the use of crystalline Form I of rosuvastatin zinc (2:1) salt of the Formula (I) for the treatment of diseases or disorders associated with lipid metabolism including hypercholesterolemia, hyperlipoproteinemia, dyslipidemia and atherosclerosis.

According to another aspect of the present invention, there is provided a method for the treatment of diseases or disorders associated with lipid metabolism, including hypercholesterolemia, hyperlipoproteinemia, dyslipidemia and atherosclerosis, which comprises administering to a patient in need of such treatment an effective amount of the crystalline Form I of rosuvastatin zinc salt (2:1) of the Formula (I).

Further aspects of the present invention are demonstrated by the following examples, without restricting the invention to said examples in any way.

Example 1

Amorphous form of 7-[4-(4-fluorophenyl)-6-isopropyl-2-(methanesulfonyl-methyl-amino)-pyrimidin-S-yl]-(3R,5S)-dihydroxy-hept-6-enoic acid zinc salt (2:1)

50.0 g (0.09 mol) of 7-[4-(4-fluorophenyl)-6-isopropyl-2-(methanesulfonyl-methyl-amino)-pyrimidin-5-yl]-(3R,5S)-dihydroxyhept-6-enoic acid tert-butylamine salt are dissolved in the mixture of 500 cm$^3$ of ethyl acetate and 153 cm$^3$ of distilled water by stirring at the temperature of 25° C. Thereafter, into the thus obtained mixture comprising two layers 55 cm$^3$ of 2.23 M zinc sulfate solution (corresponding to 0.122 mol ZnSO4 monohydrate) are added in 15 minutes at the temperature of 25° C. The mixture is stirred for an hour, the layers are separated and the organic layer is washed twice with 100 cm$^3$ of 2.23 M zinc sulfate solution each time and finally with 100 cm$^3$ of water. (During the last washing with water, 12 cm3 of ethanol are added to the mixture to obtain an easier separation of the layers).

The organic layer is dried by azeotropic distillation in vacuo at the temperature of 50° C. and at the pressure of 50 to 70 mbar (ca. 5-7 kPa) in several steps according to the following procedure.

In the first step, the solvent is distilled off almost completely. The residue is dissolved in 500 cm$^3$ of ethyl acetate at a temperature around 30° C. and the solvent is distilled off for the second time, yielding a thick, partly solidified suspension weighing 154 g. The product thus obtained is homogenized with 300 cm3 of ethyl acetate and the solvent is evaporated again until a thick suspension is formed. Thus 182.0 g of homogeneous product is obtained in the form of a suspension. This is mixed with 200 cm$^3$ of ethyl acetate and the suspension is filtered by suction. The product is suspended on the filter three times in 90 cm$^3$ of ethyl acetate each.

The solids thus obtained are dried in a vacuum drying cabinet in a thin, well-spread layer for 24 hours at the temperature of 25° C. and at the pressure of 5 mbar (approx. 5 kPa), protected from light. Subsequently the product is milled and dried again for 6 hours at 50° C. at the pressure of 5 mbar. Thus 41.74 g (90%) product are obtained.

IR (KBr): 3425 (broad), 2969, 1605, 1547, 1510, 1381, 1230, 1197, 1156, 965, 901, 844, 811, 776, 576, 567, 520 cm-1
Melting point: melting begins from 137° C.
Water content: 0.85%.

Example 2

Crystalline Form I 7-[4-(4-fluorophenyl)-6-isopropyl-2-(methanesulfonyl-methyl-amino)-pyrimidin-5-yl]-(3R,5S)-dihydroxy-hept-6-enoic acid zinc salt (2:1)

37.0 g (36.0 mmol) of amorphous rosuvastatin zinc (2:1) salt produced according to the method of Example 1 are thoroughly ground in a mortar and mixed gradually with 740 cm$^3$ of an ice-distilled water mixture in an apparatus under argon atmosphere. The suspension is stirred at the temperature of 0° C. for four hours. Thereafter the suspension is filtered, the solids are washed on the filter five times by suspending with 90 cm$^3$ of water each at the temperature of 20-22° C. and the water is removed thoroughly by suction. The wet product thus obtained is transferred into an apparatus equipped with a stirrer, 740 cm$^3$ of ice-cooled distilled water are added gradually and the suspension is stirred at the temperature of 0° C. for two hours in argon atmosphere. The cream-like suspension is filtered, the flask is rinsed with 100 cm$^3$ of distilled water and the liquid is subsequently used to wash the filtered solid.

The solid thus obtained is dried in a vacuum drying cabinet in a thin, well-spread layer for 24 hours at the temperature of 25° C. and at the pressure of 5 mbar (approx. 0.5 kPa), protected from light.

Subsequently the product is milled and dried again for 5 hours at 50° C. at the pressure of 5 mbar. Thus 31.6 g (85%) product are obtained. Powder X-ray diffractogram of the product is shown in FIG. 1.
Melting point: 119-121° C.
Purity (by HPLC): 99.78%.
Water content: 5.7%.

Example 3

Crystalline Form I of 7-[4-(4-fluorophenyl)-6-isopropyl-2-(methanesulfonyl-methyl-amino)-pyrimidin-5-yl]-(3R,5S)-dihydroxy-hept-6-enoic acid zinc salt (2:1)

69.0 g (67.2 mmol) of amorphous rosuvastatin zinc (2:1) salt prepared according to Example 1 are thoroughly ground in a mortar and transferred into a flask. 1380 cm$^3$ of aqueous solution containing 0.014 g (0.35 mmol) sodium hydroxide are added gradually at the temperature of 20° C., under argon atmosphere. The suspension is stirred at the same temperature for 4 hours, filtered, washed twice on the filter with 150 cm$^3$ of sodium hydroxide solution (0.35 mmol/1380 cm$^3$) each and most of the water is removed by suction. The wet product thus obtained is transferred to the apparatus, stirred with 1380 cm$^3$ of aqueous solution containing 0.014 g (0.35 mmol) sodium hydroxide at 20° C. for 2 hours. The thick suspension is filtered, the flask is rinsed with sodium hydroxide solution (0.35 mmol/1380 cm$^3$) which is subsequently used for washing the filtered solids.

The product thus obtained is spread carefully in a thin layer, dried in a vacuum drying cabinet for 40 hours at 25-27° C. and at the pressure of i5 mbar, protected from light. Thus 60.03 g (87%) product is obtained, which has identical X-ray diffractogram with that of the product obtained in Example 2.
Melting point: 119-121° C.
Purity (by HPLC): 99.71%.
Water content: 5.4%.

Example 4

Crystalline Form I of 7-[4-(4-fluorophenyl)-6-isopropyl-2-(methanesulfonyl-methyl-amino)-pyrimidin-5-yl]-(3R,5S)-dihydroxy-hept-6-enoic acid zinc salt (2:1)

0.30 g (29 mmol) of amorphous rosuvastatin zinc salt (2:1) prepared according to the method of Example 1 are added to 3 cm$^3$ of isopropyl acetate and 3 cm$^3$ of water under stirring. The reaction mixture comprising two layers is stirred for 1 week at the temperature of 25° C., filtered and dried in a vacuum drying cabinet at 25-27° C. and at the pressure of 5 mbar for 24 hours, protected from light. Thus 0.26 g (87%) product having identical X-ray diffractogram to that of the product of Example 2 are obtained.
Melting point: 119-121° C.

What we claim is:

1. Crystalline Form I rosuvastatin zinc (2:1) salt of the Formula I

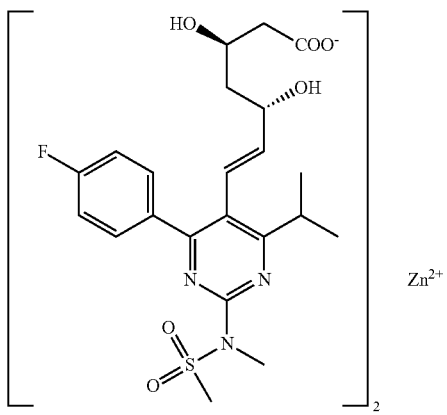

(I)

having an X-ray powder diffractogram containing the specific diffraction angles of 6.621; 19.089; and 22.466 degrees 2θ measured by using the Cu$_{Kα}$ radiation.

2. Crystalline Form I rosuvastatin zinc (2:1) salt of the Formula (I) according to claim 1 having an X-ray powder diffractogram containing the specific diffraction angles of 6.621; 18.756; 19.089; 19.505; 22.466 degrees 2Θ measured by using the Cu$_{Kα}$ radiation.

3. Crystalline Form I rosuvastatin zinc (2:1) salt of the Formula (I) according to claim 1 having an X-ray powder diffractogram containing the specific diffraction angles of 6.621; 9.920; 11.213; 13.248; 16.127; 16.471; 17.230; 18.756; 19.089; 19.505; 22.101; 22.466 degrees 2θ measured by using the Cu$_{Kα}$ radiation.

4. Crystalline Form I rosuvastatin zinc (2:1) salt of the Formula (I) according to claim 1, characterized by the X-ray diffractogram demonstrated in FIG. 1 and having the following specific diffraction data:

| Peak No. | 2Θ | d (Å) | Relative intensity (%) |
|---|---|---|---|
| 1 | 5.584 | 15.81321 | 22.2 |
| 2 | 5.889 | 14.99555 | 12.1 |
| 3 | 6.621 | 13.33946 | 69.1 |
| 4 | 7.038 | 12.55036 | 5.1 |
| 5 | 9.920 | 8.90897 | 29.4 |
| 6 | 11.072 | 7.98468 | 24.4 |
| 7 | 11.213 | 7.88447 | 29.5 |
| 8 | 11.679 | 7.57108 | 23.6 |
| 9 | 12.391 | 7.13765 | 10.4 |
| 10 | 13.248 | 6.67775 | 29.2 |
| 11 | 14.266 | 6.20332 | 18.7 |
| 12 | 15.311 | 5.78220 | 19.4 |
| 13 | 16.127 | 5.49159 | 31.1 |
| 14 | 16.471 | 5.37744 | 36.6 |
| 15 | 17.230 | 5.14225 | 32.2 |
| 16 | 17.936 | 4.94151 | 17.9 |
| 17 | 18.756 | 4.72726 | 59.1 |
| 18 | 19.089 | 4.64561 | 100 |
| 19 | 19.505 | 4.54752 | 50.5 |
| 20 | 20.074 | 4.41990 | 58.8 |
| 21 | 20.738 | 4.27984 | 25.9 |
| 22 | 21.217 | 4.18430 | 11 |
| 23 | 21.620 | 4.10713 | 11.3 |
| 24 | 22.101 | 4.01878 | 31.4 |
| 25 | 22.466 | 3.95434 | 76.3 |

-continued

| Peak No. | 2Θ | d (Å) | Relative intensity (%) |
|---|---|---|---|
| 26 | 22.968 | 3.86898 | 18.2 |
| 27 | 23.499 | 3.78272 | 27.4 |
| 28 | 24.372 | 3.64924 | 14 |
| 29 | 25.001 | 3.55888 | 18 |
| 30 | 25.751 | 3.45684 | 6.7 |
| 31 | 26.806 | 3.32318 | 19.7 |
| 32 | 27.243 | 3.27079 | 7.2 |
| 33 | 27.828 | 3.20337 | 7.8 |
| 34 | 28.171 | 3.16516 | 7.2 |
| 35 | 29.239 | 3.05194 | 8.5 |
| 36 | 29.885 | 2.98740 | 4.9 |
| 37 | 30.971 | 2.88504 | 6.5 |
| 38 | 31.655 | 2.82424 | 15.7 |
| 39 | 32.635 | 2.74171 | 13.1. |

5. Crystalline Form I rosuvastatin zinc salt (2:1) of the Formula (I) according to claim 1 containing 1 to 10 moles of water.

6. Crystalline Form I rosuvastatin zinc salt (2:1) of the Formula (I) according to claim 1 containing 1 to 6 moles of water.

7. Method for the preparation of crystalline Form I rosuvastatin zinc salt (2:1) of the Formula (I) according to claim 1, which comprises the steps of:
(a) stirring amorphous rosuvastatin zinc salt (2:1) in 5 to 100-fold weight of water, at a temperature between 0 and 25° C., for 4 to 168;
(b) isolating the solids and, if desired;
(c) washing and drying the crystalline product.

8. The method for the preparation of crystalline Form I rosuvastatin zinc salt (2:1) of the Formula (I) defined in claim 7 wherein step (a) is carried out in a 20 fold weight of water.

9. The method for the preparation of crystalline Form I rosuvastatin zinc salt (2:1) of the Formula (I) defined in claim 7 wherein step (a) is carried out at a temperature between 0 and 5° C.

10. The method for the preparation of crystalline Form I rosuvastatin zinc salt (2:1) of the Formula (I) defined in claim 7 wherein step (a) is carried out for 4 to 8 hours.

11. Method for the preparation of crystalline Form I rosuvastatin zinc salt (2:1) of the Formula (I) according to claim 1, which comprises the steps of:
(a) stirring amorphous rosuvastatin zinc salt (2:1) in 5 to 100-fold weight of water at a temperature between 0 and 25° C. for 2 to 168 hours;
(b) isolating the solids by filtration;
(c) washing the solids at least once with water;
(d) stirring the thus obtained solid mass in 5 to 100-fold weight of water at a temperature between 0 and 25° C. for 1 to 168 hours;
(e) isolating the crystalline product by filtration; and
(f) optionally washing and drying the obtained crystalline Form I rosuvastatin zinc (2:1) salt.

12. The method for the preparation of crystalline Form I rosuvastatin zinc salt (2:1) of the Formula (I) according to claim 11 wherein step (a) is carried out in a 20 fold weight of water.

13. The method for the preparation of crystalline Form I rosuvastatin zinc salt (2:1) of the Formula (I) according to claim 11 wherein step (a) is carried out at a temperature between 0 and 5° C.

14. The method for the preparation of crystalline Form I rosuvastatin zinc salt (2:1) of the Formula (I) according to claim 11 wherein step (a) is carried out for 4 to 8 hours.

15. The method for the preparation of crystalline Form I rosuvastatin zinc salt (2:1) of the Formula (I) according to claim 11 wherein step (d) is carried out in a 20 fold weight of water.

16. The method for the preparation of crystalline Form I rosuvastatin zinc salt (2:1) of the Formula (I) according to claim 11 wherein step (d) is carried out at a temperature between 0 and 5° C.

17. The method for the preparation of crystalline Form I rosuvastatin zinc salt (2:1) of the Formula (I) according to claim 11 wherein step (d) is carried out for 2 to 4 hours.

18. Method for the preparation of crystalline Form I rosuvastatin zinc salt (2:1) of the Formula (I) according to claim 1, which comprises the steps of:
 (a) stirring amorphous rosuvastatin zinc salt (2:1) in 5 to 100-fold weight of an aqueous solution of 0.0005-0.01 molar equivalent of an alkali metal hydroxide, calculated for the molar amount of rosuvastatin zinc salt of the Formula (I) for 4 to 168 hours at a temperature between 0 to 25° C.,
 (b) isolating the solid product by filtration and if desired;
 (c) washing and drying the product.

19. The method for the preparation of crystalline Form I rosuvastatin zinc salt (2:1) of the Formula (I) according to claim 18, wherein step (a) is carried out at 20° C.

20. Method for the preparation of crystalline Form I rosuvastatin zinc (2:1) salt of the Formula (I) according to claim 1, which comprises the steps of:
 (a) stirring amorphous rosuvastatin zinc salt (2:1) in 5 to 100-fold weight of an aqueous solution of 0.0005-0.01 molar equivalent of an alkali metal hydroxide, calculated for the molar amount of rosuvastatin zinc salt of the Formula (I), for 4 to 168 hours at a temperature between 0 to 25° C.;
 (b) isolating the solid product by filtration;
 (c) washing the isolated solid with a solution of 0.0005-0.01 molar equivalents of alkali metal hydroxide in 5 to 100-fold weight of water to the amount of rosuvastatin zinc (2:1) salt at least once;
 (d) stirring the thus obtained solid in 5 to 100-fold weight of an aqueous solution of 0.0005-0.01 molar equivalents of an alkali metal hydroxide, calculated for the molar amount of rosuvastatin zinc salt of the Formula (I) for 1 to 168 hours, at a temperature between 0 to 25° C.;
 (e) isolating the solid product by filtration, and if desired;
 (f) washing and drying the crystalline Form I rosuvastatin zinc (2:1) salt.

21. Medicament containing a therapeutically effective amount of crystalline Form I rosuvastatin zinc (2:1) salt according to claim 1 admixed with a pharmaceutically acceptable vehicle or auxiliary agent.

22. Method for the treatment of diseases or disorders associated with lipid-metabolism including hypercholesterolemia, hyperlipoproteinemia, dyslipidemia or atherosclerosis, which comprises administering to a patient in need of said treatment a medicament containing a therapeutically effective amount of crystalline Form rosuvastatin zinc (2:1) salt according to claim 21.

* * * * *